United States Patent
Suleiman et al.

(10) Patent No.: US 11,434,204 B2
(45) Date of Patent: *Sep. 6, 2022

(54) METHOD FOR PRODUCING A POLYMORPHIC FORM OF 3-[5-AMINO-4-(3-CYANOBENZOYL)-PYRAZOL-1-YL]-N-CYCLOPROPYL-4-METHYLBENZAMIDE

(71) Applicant: MEREO BIOPHARMA 1 LIMITED, London (GB)

(72) Inventors: Osama Suleiman, Cambridge (GB); Lucia Romero Perez, Royston (GB); Cornelius Stephan Harlacher, Reinach (CH); Stewart Jones, London (GB)

(73) Assignee: MEREO BIOPHARMA 1 LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/149,649

(22) Filed: Jan. 14, 2021

(65) Prior Publication Data

US 2021/0206726 A1 Jul. 8, 2021

Related U.S. Application Data

(63) Continuation of application No. 16/317,012, filed as application No. PCT/GB2017/052056 on Jul. 13, 2017, now Pat. No. 10,934,260.

(30) Foreign Application Priority Data

Jul. 14, 2016 (GB) .................... 1612240

(51) Int. Cl.
*C07D 231/18* (2006.01)

(52) U.S. Cl.
CPC ........ *C07D 231/18* (2013.01); *C07B 2200/13* (2013.01)

(58) Field of Classification Search
CPC .................................................. C07D 231/18
See application file for complete search history.

(56) References Cited

U.S. PATENT DOCUMENTS

| 7,863,314 | B2 | 1/2011 | Fryszman et al. |
| 8,242,117 | B2 | 8/2012 | Fryszman et al. |
| 8,410,160 | B2 | 4/2013 | Fryszman et al. |
| 8,580,838 | B2 | 11/2013 | Fryszman et al. |
| 9,339,491 | B2 | 5/2016 | Ford |
| 10,603,306 | B2 | 3/2020 | Orford et al. |
| 10,617,674 | B2 | 4/2020 | Orford et al. |
| 10,934,260 | B2 * | 3/2021 | Suleiman ................ A61P 29/00 |

FOREIGN PATENT DOCUMENTS

| WO | 1999/057101 A1 | 11/1999 |
| WO | 2005/009973 A1 | 2/2005 |
| WO | 2013/139809 A1 | 9/2013 |

OTHER PUBLICATIONS

International Search Report and Written Opinion issued in PCT/GB2017/052055 dated Sep. 6, 2017 (13 pages).
International Search Report and Written Opinion issued in PCT/GB2017/052056 dated Sep. 6, 2017 (13 pages).
Bernstein, J. "Polymorphism of molecular crystals" Moscow, Nauka, 2007, chapter 7.3.2. Bioavailability pp. 244-250.
Caira, Mino R, "Crystalline Polymorphism of Organic Compounds", Topics in Current Chemistry, Springer. Berlin, DE, vol. 198, Jan. 1, 1998 (Jan. 1, 1998), pp. 163-208.
Morissette et al., "High-throughput crystallization: polymorphs, salts, co-crystals and solvates of pharmaceutical solids", Advanced drug delivery reviews, 2004, v. 56, pp. 275-300.
Yu, Lian, "Amorphous Pharmaceutical Solids: preparation, characterization and stabilization," Advanced Drug Delivery Reviews 28 (2001) pp. 27-42.
Brittain, Harry G., "X-ray Diffraction III: Pharmaceutical Applications of X-ray Powder Diffraction", Spectroscopy, 16(7):14-18 (2001).
Lee, Eun Hee, "A practical guide to pharmaceutical polymorph screening & selection", Asian Journal of Pharmaceutical Sciences, 9:163-175 (2014).

* cited by examiner

*Primary Examiner* — Matthew P Coughlin
(74) *Attorney, Agent, or Firm* — Wolff IP a Prof Corp; Jessica Wolff

(57) ABSTRACT

This invention relates to a process for the preparation of Form A of 3-[5-amino-4-(3-cyanobenzoyl)-pyrazol-1-yl]-N-cyclopropyl-4-methylbenzamide. Also disclosed herein is Form A of 3-[5-amino-4-(3-cyanobenzoyl)-pyrazol-1-yl]-N-cyclopropyl-4-methylbenzamide, or pharmaceutical compositions thereof, obtainable by the process described herein.

6 Claims, 6 Drawing Sheets

METHOD FOR PRODUCING A POLYMORPHIC FORM OF 3-[5-AMINO-4-(3-CYANOBENZOYL)-PYRAZOL-1-YL]-N-CYCLOPROPYL-4-METHYLBENZAMIDE

CROSS-REFERENCE TO RELATED APPLICATIONS

The present invention is a continuation of U.S. patent application Ser. No. 16/317,012, filed Jan. 10, 2019, which is the U.S. national phase of International Patent Application No. PCT/GB2017/052056, filed Jul. 13, 2017, which designated the United States, and which claims priority to Great Britain Patent Application No. 1612240.0, filed Jul. 14, 2016, each of which is hereby incorporated by reference in its entirety including all tables, figures, and claims.

FIELD

Disclosed herein are methods for selectively producing particular crystal polymorphs of the compound 3-[5-amino-4-(3-cyanobenzoyl)-pyrazol-1-yl]-N-cyclopropyl-4-methylbenzamide.

DESCRIPTION OF RELATED ART

Solids exist in either amorphous or crystalline forms. In the case of crystalline forms, molecules are positioned in 3-dimensional lattice sites. Crystallization of solids from solution is known in the art, for example by mixing the desired compound in an appropriate amount of solvent or mixture of solvents, heating to achieve dissolution, and cooling to precipitate the product.

When a compound recrystallizes from a solution or slurry, it may crystallize with different spatial lattice arrangements, a property referred to as "polymorphism", with the different crystal forms individually being referred to as a "polymorph". Different polymorphic forms of a given substance may also differ from each other with respect to one or more physical properties, such as solubility, true density, crystal shape, compaction behaviour, flow properties, and/or solid state stability.

In the case of a chemical substance that exists in two (or more) polymorphic forms having different thermodynamic stabilities, the more unstable forms generally convert to the more thermodynamically stable forms at a given temperature after a sufficient period of time. When this transformation is not rapid, the thermodynamically unstable form is referred to as the "metastable" form. In general, the stable form exhibits the highest melting point, the lowest solubility, and the maximum chemical stability of the different polymorphic forms. However, the metastable form may exhibit sufficient chemical and physical stability under normal storage conditions to permit its use in a commercial form. Furthermore, the metastable form, although less stable than the most thermodynamically stable polymorphic form, may exhibit properties that are more desirable than those of the more stable form, such as better formulative ability, improved dispersability in water, and the like.

It has been discovered that the compound 3-[5-amino-4-(3-cyanobenzoyl)-pyrazol-1-yl]-N-cyclopropyl-4-methylbenzamide exists in a large number of polymorphic forms. Many of these forms are undesirable from the point of view of producing pharmaceutically acceptable compositions. This is for a variety of reasons, including lack of stability, high hygroscopicity, low aqueous solubility and handling difficulty.

SUMMARY OF INVENTION

The presently disclosed crystallization methods allow for selectively controlling the crystallization of polymorphic forms of 3-[5-amino-4-(3-cyanobenzoyl)-pyrazol-1-yl]-N-cyclopropyl-4-methylbenzamide. Specifically, the present invention involves a method for the production of a particular polymorphic form of 3-[5-amino-4-(3-cyanobenzoyl)-pyrazol-1-yl]-N-cyclopropyl-4-methylbenzamide hereinafter designated Form A.

Recrystallization of 3-[5-amino-4-(3-cyanobenzoyl)-pyrazol-1-yl]-N-cyclopropyl-4-methylbenzamide from a range of various solvents leads to mixtures of different polymorphic forms, including solvates, hydrated, anhydrates and the like. If the other polymorphic forms of 3-[5-amino-4-(3-cyanobenzoyl)-pyrazol-1-yl]-N-cyclopropyl-4-methylbenzamide obtained during recrystallisation cannot be converted to Form A, then it must be disposed of, resulting in lost revenue and inefficient production processes.

Form A has particular advantages in terms of pharmaceutical formulation and handling. Form A is particularly advantageous as it in non-hygroscopic and the methods of the present invention produce a free flowing powder which is easy to handle and process to produce pharmaceutical formulations including 3-[5-amino-4-(3-cyanobenzoyl)-pyrazol-1-yl]-N-cyclopropyl-4-methylbenzamide.

To date, there are no simple methods for controlling the crystallization of polymorphic forms of 3-[5-amino-4-(3-cyanobenzoyl)-pyrazol-1-yl]-N-cyclopropyl-4-methylbenzamide. There is thus an urgent and unmet need in the art for an efficient method for selectively controlling the crystallization of polymorphic forms of 3-[5-amino-4-(3-cyanobenzoyl)-pyrazol-1-yl]-N-cyclopropyl-4-methylbenzamide.

It has been found that embodiments disclosed herein satisfy this heretofore unmet need in that they provide a process for selectively controlling the crystallization of polymorphic forms of 3-[5-amino-4-(3-cyanobenzoyl)-pyrazol-1-yl]-N-cyclopropyl-4-methylbenzamide. In particular, the presently claimed methods allow improved control of particle properties, such as particle size, enable improved yields of specific polymorphs and reduce contamination by residual solvents.

In a first aspect, there is provided a process for the preparation of a crystalline polymorph Form A of 3-[5-amino-4-(3-cyanobenzoyl)-pyrazol-1-yl]-N-cyclopropyl-4-methylbenzamide, comprising:
 (a) dissolving 3-[5-amino-4-(3-cyanobenzoyl)-pyrazol-1-yl]-N-cyclopropyl-4-methylbenzamide, at a temperature of at least 40° C., in a non-aqueous solvent or mixture of non-aqueous solvents to obtain a solution, wherein the solvent or solvents contain less than about 5 wt % of water relative to the 3-[5-amino-4-(3-cyanobenzoyl)-pyrazol-1-yl]-N-cyclopropyl-4-methylbenzamide starting material;
 (a') optionally seeding the solution with Form A crystals of 3-[5-amino-4-(3-cyanobenzoyl)-pyrazol-1-yl]-N-cyclopropyl-4-methylbenzamide;
 (b) cooling the solution, thereby forming crystals of polymorph Form A of 3-[5-amino-4-(3-cyanobenzoyl)-pyrazol-1-yl]-N-cyclopropyl-4-methylbenzamide;
 (c) isolating the crystals.

In a second aspect, there is provided a process for the preparation of a crystalline polymorph Form A of 3-[5-amino-4-(3-cyanobenzoyl)-pyrazol-1-yl]-N-cyclopropyl-4-methylbenzamide, comprising:

(a) dissolving 3-[5-amino-4-(3-cyanobenzoyl)-pyrazol-1-yl]-N-cyclopropyl-4-methylbenzamide, at a temperature of at least 40° C., in a non-aqueous solvent or mixture of non-aqueous solvents to obtain a solution;

(a') optionally seeding the solution with Form A crystals of 3-[5-amino-4-(3-cyanobenzoyl)-pyrazol-1-yl]-N-cyclopropyl-4-methylbenzamide;

(b) cooling the solution, thereby forming crystals of polymorph Form A of 3-[5-amino-4-(3-cyanobenzoyl)-pyrazol-1-yl]-N-cyclopropyl-4-methylbenzamide;

(c) isolating the crystals;

wherein the temperature of all process steps does not exceed 100° C.

In a third aspect, there is provided a process for the preparation of a crystalline polymorph Form A of 3-[5-amino-4-(3-cyanobenzoyl)-pyrazol-1-yl]-N-cyclopropyl-4-methylbenzamide, comprising:

(a) dissolving 3-[5-amino-4-(3-cyanobenzoyl)-pyrazol-1-yl]-N-cyclopropyl-4-methylbenzamide, at a temperature of at least 40° C., in a non-aqueous solvent or mixture of non-aqueous solvents to obtain a solution, wherein the solvent or solvents contain less than about 5 wt % of water relative to the 3-[5-amino-4-(3-cyanobenzoyl)-pyrazol-1-yl]-N-cyclopropyl-4-methylbenzamide starting material;

(a') optionally seeding the solution with Form A crystals of 3-[5-amino-4-(3-cyanobenzoyl)-pyrazol-1-yl]-N-cyclopropyl-4-methylbenzamide;

(b) cooling the solution, thereby forming crystals of polymorph Form A of 3-[5-amino-4-(3-cyanobenzoyl)-pyrazol-1-yl]-N-cyclopropyl-4-methylbenzamide;

(c) isolating the crystals;

wherein the temperature of all process steps does not exceed 100° C.

During the manufacturing process, Form A is produced in an acceptable yield when 3-[5-amino-4-(3-cyanobenzoyl)-pyrazol-1-yl]-N-cyclopropyl-4-methylbenzamide is recrystallised in non-aqueous solution. In the presence of greater than about 5% water, relative to the weight of the 3-[5-amino-4-(3-cyanobenzoyl)-pyrazol-1-yl]-N-cyclopropyl-4-methylbenzamide subject to recrystallisation, a hydrate of 3-[5-amino-4-(3-cyanobenzoyl)-pyrazol-1-yl]-N-cyclopropyl-4-methylbenzamide is formed in unacceptable quantities, which has a different polymorphic form to Form A, thereby constituting an impurity.

During the manufacturing process, Form A is produced in an acceptable yield when 3-[5-amino-4-(3-cyanobenzoyl)-pyrazol-1-yl]-N-cyclopropyl-4-methylbenzamide is recrystallised at temperatures not exceeding 100° C. If this temperature is exceeded, a different polymorphic form of 3-[5-amino-4-(3-cyanobenzoyl)-pyrazol-1-yl]-N-cyclopropyl-4-methylbenzamide (designated Form B) is formed in unacceptable quantities, thereby constituting an impurity.

BRIEF DESCRIPTION OF DRAWINGS

Certain aspects of the embodiments described herein may be more clearly understood by reference to the drawings, which are intended to illustrate, but not limit, the invention, and wherein.

DETAILED DESCRIPTION OF SPECIFIC EMBODIMENTS

Figure 1:
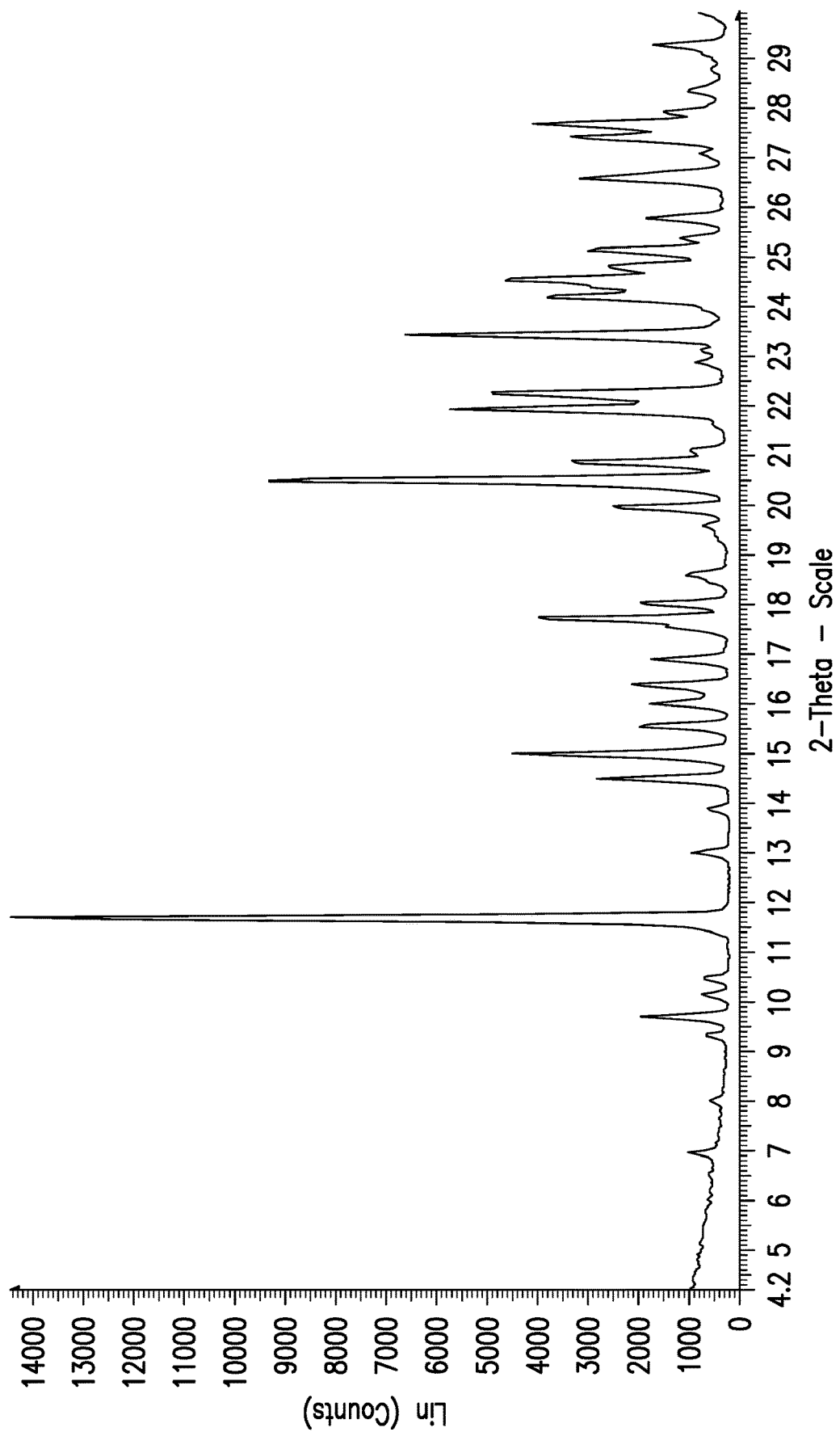
FIG. 1 is the XRPD spectrum of Form A polymorph of 3-[5-amino-4-(3-cyanobenzoyl)-pyrazol-1-yl]-N-cyclopropyl-4-methylbenzamide.
Figure 2:
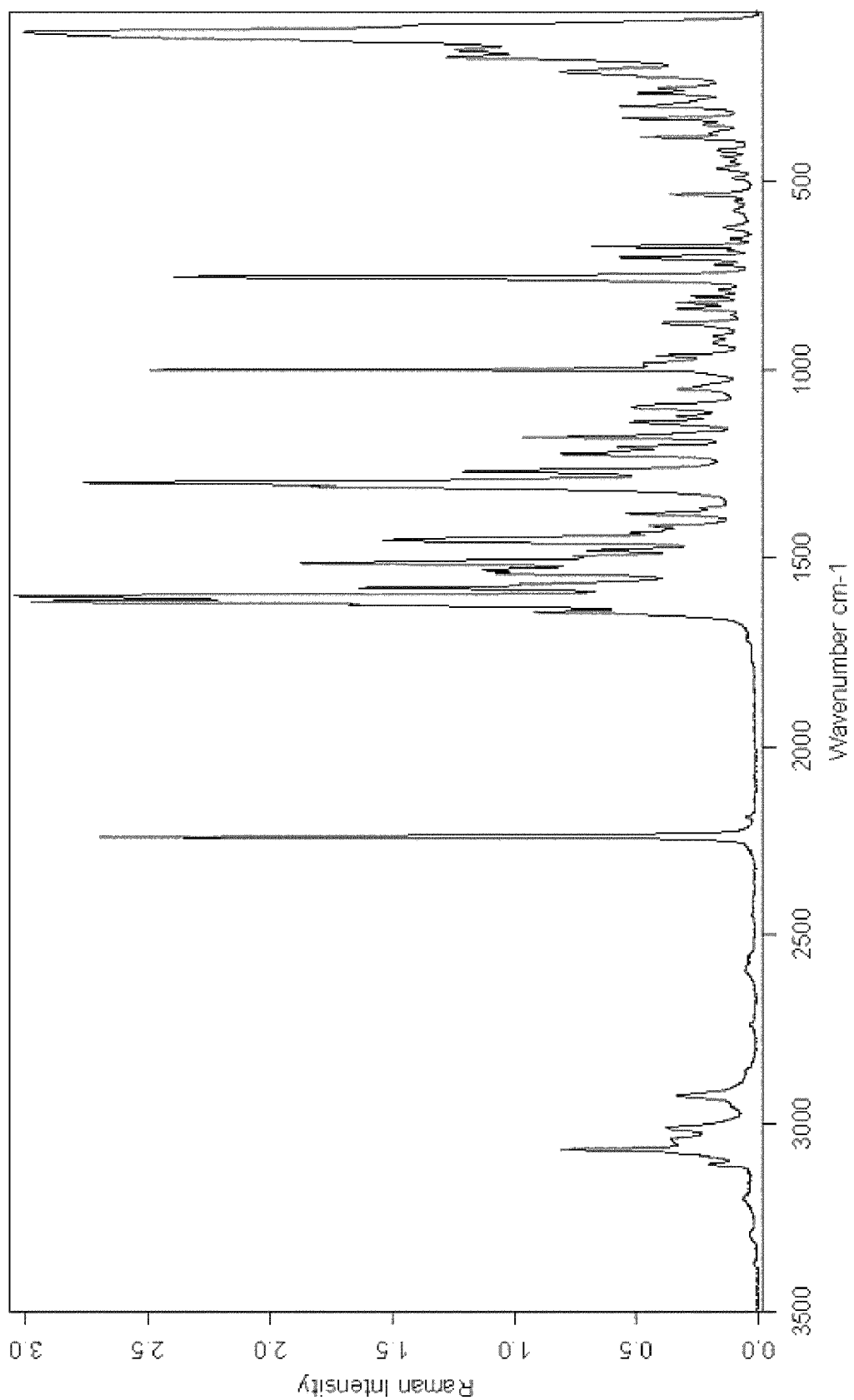
FIG. 2 is the Raman spectrum of Form A polymorph of 3-[5-amino-4-(3-cyanobenzoyl)-pyrazol-1-yl]-N-cyclopropyl-4-methylbenzamide.
Figure 3:
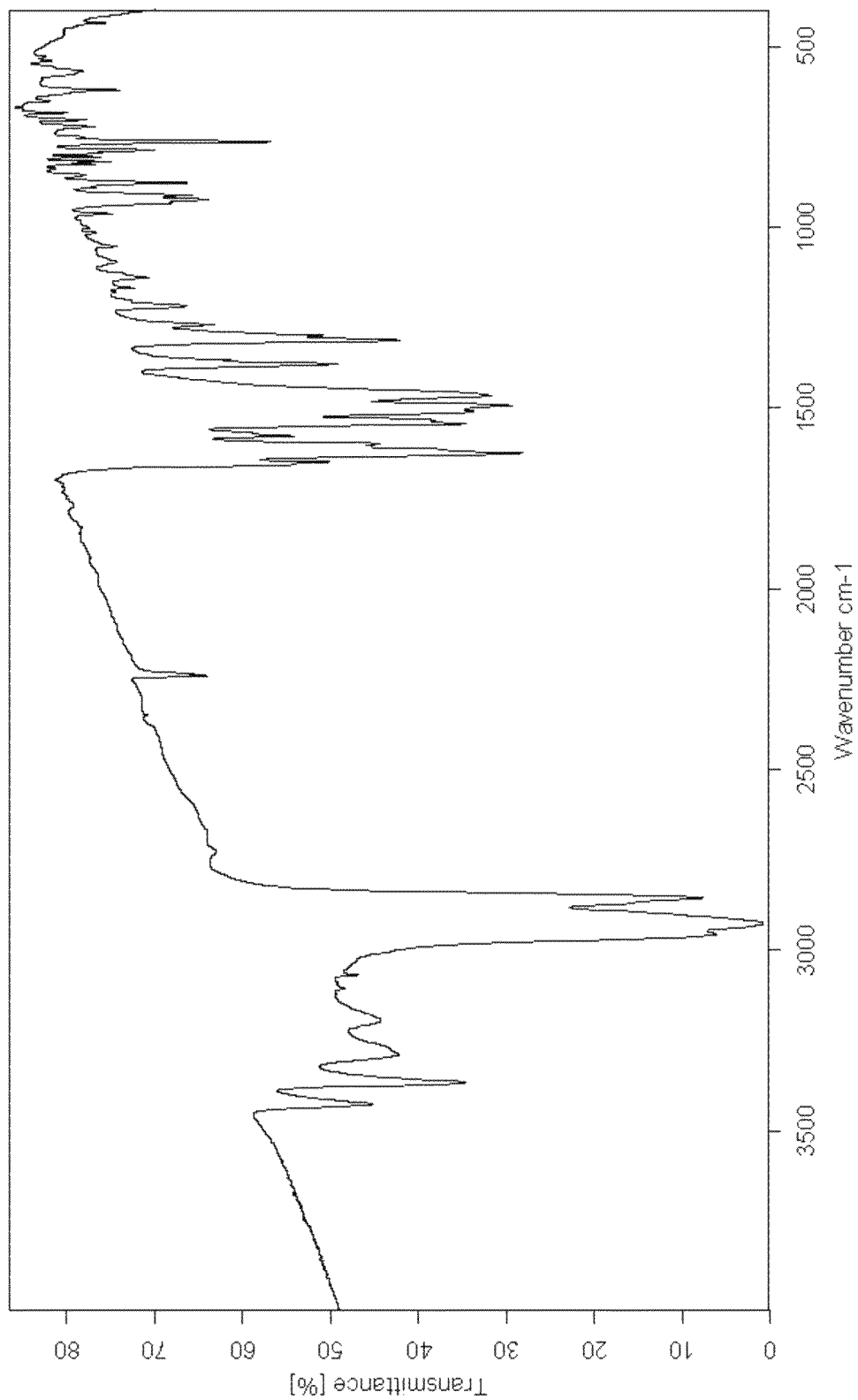
FIG. 3 is an FT-IR spectrum of Form A polymorph of 3-[5-amino-4-(3-cyanobenzoyl)-pyrazol-1-yl]-N-cyclopropyl-4-methylbenzamide.

The starting material for any aspect of the invention may be any source of 3-[5-amino-4-(3-cyanobenzoyl)-pyrazol-1-yl]-N-cyclopropyl-4-methylbenzamide. For example the starting material for the method of producing Form A according to the present invention may be selected from the group consisting of crude, amorphous, polymorphic (other than pure Form A), a mixture of polymorphs of 3-[5-amino-4-(3-cyanobenzoyl)-pyrazol-1-yl]-N-cyclopropyl-4-methylbenzamide, and mixtures thereof. For example, the 3-[5-amino-4-(3-cyanobenzoyl)-pyrazol-1-yl]-N-cyclopropyl-4-methylbenzamide starting material used for preparing Form A according to the disclosed process in WO 2005/009973 (such as Example 161 thereof).

The methods of any of the aspects of the present invention produce pure Form A 3-[5-amino-4-(3-cyanobenzoyl)-pyrazol-1-yl]-N-cyclopropyl-4-methylbenzamide.

As used herein, "pure form A" means crystalline polymorphic Form A having less than 10% by weight of any other polymorphic form of 3-[5-amino-4-(3-cyanobenzoyl)-pyrazol-1-yl]-N-cyclopropyl-4-methylbenzamide, preferably less than 5% by weight, preferably less than 2% by weight, preferably less than 1% by weight, preferably less than 0.5% by weight, preferably less than 0.1% by weight of other polymorphic forms of 3-[5-amino-4-(3-cyanobenzoyl)-pyrazol-1-yl]-N-cyclopropyl-4-methylbenzamide.

The powder XRD patterns and data for polymorphic form A is distinctly different to other polymorphic forms of 3-[5-amino-4-(3-cyanobenzoyl)-pyrazol-1-yl]-N-cyclopropyl-4-methylbenzamide. Form A exhibits an X-ray powder diffraction pattern substantially as given in Table 1, having characteristic peaks (expressed in degrees 2 (+/−0.2° θ) at one or more of the following positions:

| Angle-2-Theta ° | Intensity |
| --- | --- |
| 9.3 | 4.6 |
| 9.7 | 13.7 |
| 10.2 | 5.4 |
| 10.5 | 5.1 |
| 11.7 | 100. |
| 13.0 | 6.6 |
| 14.5 | 19.7 |
| 15.0 | 31.6 |
| 15.5 | 14.0 |
| 16.0 | 12.5 |
| 16.4 | 14.9 |
| 16.9 | 12.3 |
| 17.8 | 27.9 |

-continued

| Angle-2-Theta ° | Intensity |
|---|---|
| 18.0 | 13.9 |
| 20.0 | 17.6 |
| 20.5 | 64.4 |
| 20.9 | 23.1 |
| 22.0 | 39.9 |
| 22.3 | 34.1 |
| 23.4 | 45.8 |
| 24.2 | 26.3 |
| 24.5 | 32.2 |

Useful formulations of compositions containing Form A can be prepared in conventional ways. These include preparation as dusts, pellets, solutions, suspensions, emulsions, wettable powders, and the like.

In one embodiment, Form A 3-[5-amino-4-(3-cyanobenzoyl)-pyrazol-1-yl]-N-cyclopropyl-4-methylbenzamide can be prepared by crystallizing 3-[5-amino-4-(3-cyanobenzoyl)-pyrazol-1-yl]-N-cyclopropyl-4-methylbenzamide from a non-aqueous solvent or mixture of solvents.

In a preferred embodiment according to any of the above aspects of the invention, the process includes preparing a nonaqueous solution of the 3-[5-amino-4-(3-cyanobenzoyl)-pyrazol-1-yl]-N-cyclopropyl-4-methylbenzamide in one or more of the aforementioned nonaqueous solvent or mixture of solvents by applying heat until dissolution is complete, but not exceeding a temperature of 100° C., then cooling the aqueous solution slowly, preferably at a cooling rate of about between 1 and 0.01° C./min, preferably between 0.5 and 0.05° C./min, preferably between 0.2 and 0.08° C./min, preferably at about 0.1° C./min. The selection of this cooling rate helps to improve the yield of Form A and the purity of Form A in the crystalline product.

In particular, any of the above numbered aspects of the invention are capable of producing Form A crystals in a purity of greater than 80 wt % of the final crystalline material, usually greater than 90 wt %, preferably greater than 95 wt %, for example, greater than 98 wt % of the final crystalline material.

The optional seeding step (a') in any of the above numbered aspects of the invention is preferably seeded with greater than 0.1 wt % of Form A 3-[5-amino-4-(3-cyanobenzoyl)-pyrazol-1-yl]-N-cyclopropyl-4-methylbenzamide, relative to the weight of the 3-[5-amino-4-(3-cyanobenzoyl)-pyrazol-1-yl]-N-cyclopropyl-4-methylbenzamide dissolved in step (a), preferably greater than 1 wt %, preferably greater than 3 wt %, preferably greater than 4 wt %.

When seeding is used, it is generally for large scale production (greater than 5 kg) of material. The Form A seeds are preferably produced by the methods recited herein, or are obtained by separating Form A crystals from the mixture of crystals produced according to the prior art methods. Form A crystals are readily characterised and identified by their XRPD spectrum.

In a preferred embodiment according to any of the above aspects of the invention, preferably the temperature used during the crystallisation does not exceed 80° C., preferably does not exceed 70° C., preferably does not exceed 60° C., preferably does not exceed 50° C. Preferably, the temperature used during the crystallisation is greater than 40° C. As the temperature increases towards and exceeds 70° C., the amount of Form B polymorph increases, particularly with increased time spent at the higher temperature.

Thus, preferably the solution of 3-[5-amino-4-(3-cyanobenzoyl)-pyrazol-1-yl]-N-cyclopropyl-4-methylbenzamide is not exposed to temperatures of greater than 70° C. for more than 24 hours, preferably not more than 12 hours, preferably not more than 6 hours. This is demonstrated in the following table, where different solvents are tested at different temperatures.

| Temperature | Solvent | Final polymorph | Duration |
|---|---|---|---|
| 80° C. | EtOH | B | 2 days |
|  | n-PrOH | B | 2 days |
|  | i-PrOH | B | 2 days |
|  | i-BuOH | B | 2 days |
| 70° C. | EtOH | A + B | 3 days |
|  | n-PrOH | A + B | 3 days |
|  | i-PrOH | A | 3 days |
|  | i-BuOH | A | 3 days |
| 60° C. | EtOH | A | 1 day |
|  | n-PrOH | A | 1 day |
|  | i-PrOH | A | 1 day |
|  | i-BuOH | A | 1 day |
|  | DMAC/$H_2O$ = 1/1 | hydrate | 1 day |
|  | $H_2O$ | hydrate | 1 day |

Thus, it can be seen that at the higher temperatures of 70 and 80° C., conversion to Form B is effected, or a mixture of Form A and Form B are produced, particularly over longer periods of time. It can also be seen that the hydrate is formed when water is included in the solvent.

As used herein, the term "nonaqueous solvent or mixture of non-aqueous solvents" means one or more solvents selected from the group consisting of $C_{1-6}$ alcohols, $C_{4-10}$ cyclic ethers, $C_{1-6}$ nitriles, $C_{1-6}$ haloalkanes, $C_{1-6}$ ketones, dialkylformamides, dialkyl sulfoxides, $C_{3-10}$ aryls, $C_{5-10}$ alkanes, petroleum ether, $C_{1-6}$ alkyl acetate, $C_{1-6}$ ether, preferably in the substantial absence of water.

Preferred nonaqueous solvents are selected from the group consisting of methanol, ethanol, tetrahydrofuran, acetonitrile, methylene chloride, isopropyl alcohol, acetone, N,N-dimethylformamide (DMF), dimethyl sulfoxide (DMSO), toluene, benzene, n-hexane, petroleum ether, ethyl acetate, ether, dichloromethane, chloroform and carbon tetrachloride, preferably in the substantial absence of water.

Particularly preferred nonaqueous solvents are selected from the group consisting of methanol, ethanol, isopropyl alcohol and isobutanol, preferably in the substantial absence of water.

During step (b) of any of the above numbered aspects of the invention, an anti-solvent may be added to encourage precipitation of the desired crystals. Preferred anti-solvents include $C_{1-6}$ ethers and $C_{1-6}$ nitroalkanes, such as t-butyl methyl ether and nitromethane. However, the skilled person will readily be able to select an anti-solvent depending on what solvent is used in the process.

The anti-solvent:solvent ratio is preferably in the range of 0.1:1-1:0.1.

As used herein, the term "substantial absence of water" means less than 5 wt %, relative to the 3-[5-amino-4-(3-cyanobenzoyl)-pyrazol-1-yl]-N-cyclopropyl-4-methylbenzamide used in the process, preferably less than 1 wt %, preferably less than 0.5 wt %, preferably less than 0.1 wt %, preferably less than 0.05 wt %, preferably less than 0.001 wt %. The yield of Form A decreases in a linear manner above about 1 wt % water, hence, it is particularly advantageous to maintain a water concentration below 1 wt %.

The methods of the present invention conveniently produce Form A 3-[5-amino-4-(3-cyanobenzoyl)-pyrazol-1-yl]-N-cyclopropyl-4-methylbenzamide having a $D_{50}$ particle size of less than 400 μm, preferably less than 300 μm, preferably less than 200 μm.

The methods of the present invention conveniently produce Form A 3-[5-amino-4-(3-cyanobenzoyl)-pyrazol-1-yl]-N-cyclopropyl-4-methylbenzamide having a $D_{10}$ particle size of greater than 10 μm.

The crystals of Form A are isolated by any conventional method known in the art, for example by filtration, centrifugation, etc. They may be dried in an oven, and/or a vacuum drier.

Prior to or during any of the cooling steps according to any of the above numbered aspects of the invention, the amount of the solvent may be reduced, for example, by distillation, to concentrate the solution of the 3-[5-amino-4-(3-cyanobenzoyl)-pyrazol-1-yl]-N-cyclopropyl-4-methylbenzamide.

The invention will now be described further by reference to the following examples, which are intended to illustrate, but not limit, the scope of the appended claims.

Example 1

Form A Process Description

3-[5-amino-4-(3-cyanobenzoyl)-pyrazol-1-yl]-N-cyclopropyl-4-methylbenzamide was dissolved in ethanol at 75° C. The obtained solution is filtered over a particle filter to a second reactor. After cooling down to IT (Internal Temperature)=40° C. a seed suspension of 3-[5-amino-4-(3-cyanobenzoyl)-pyrazol-1-yl]-N-cyclopropyl-4-methylbenzamide in ethanol is added. The reaction mixture is kept for additional 2 hours at IT=40° C., before starting a slow cooling ramp (0.1 K/min) to IT=−10° C. The suspension is kept for at least 5 hours at IT=−10° C. The product is isolated on a filter dryer. The filter cake is washed over the reactor by using ethanol in 3 portions without stirring. Drying of the wet filter cake is performed in two operational steps. The first step is done in 5 hours at JT (Jacket Temperature)=50° C. and pressure=10-20 mbar. During this step the stirrer is not in use. The second step is done in 5 hours at JT=60° C. and pressure=10-20 mbar. During this step the stirrer is turned on for 1 min and put for 14 minutes on hold. After this period the content of ethanol ≤0.5%-m/m is fulfilled. No cleaning of the reaction vessel between the batches was required.

Figure 4A:
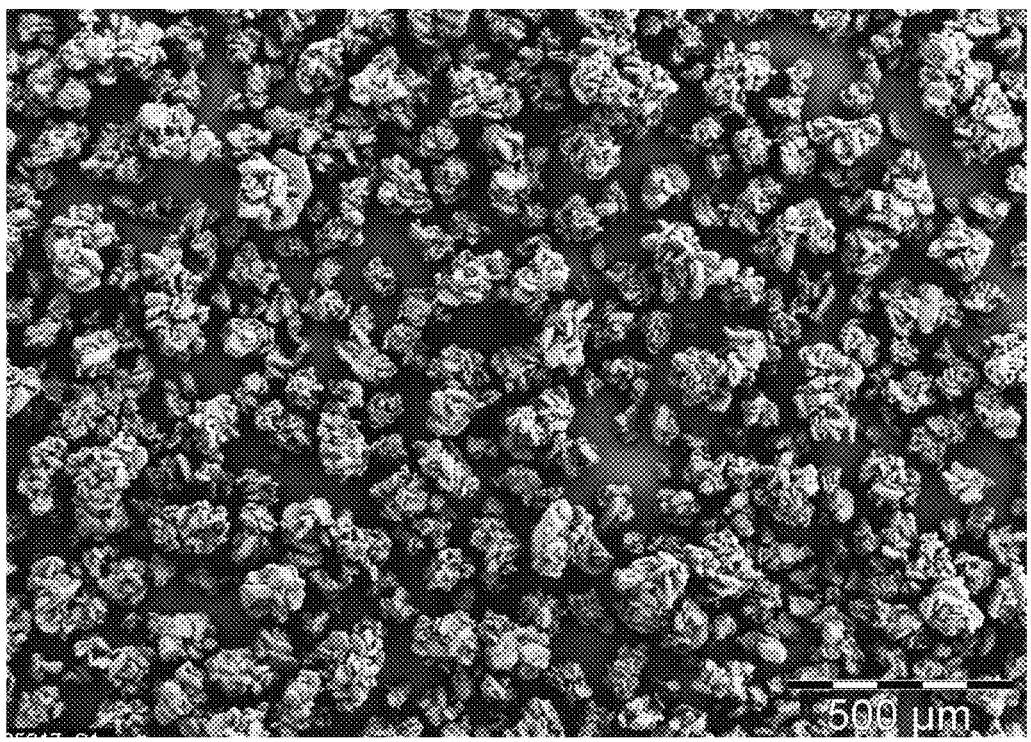
FIGS. 4a and 4b are SEM images of free flowing Form A 3-[5-amino-4-(3-cyanobenzoyl)-pyrazol-1-yl]-N-cyclopropyl-4-methylbenzamide recrystallised by the method of the present invention.
Figure 4B:
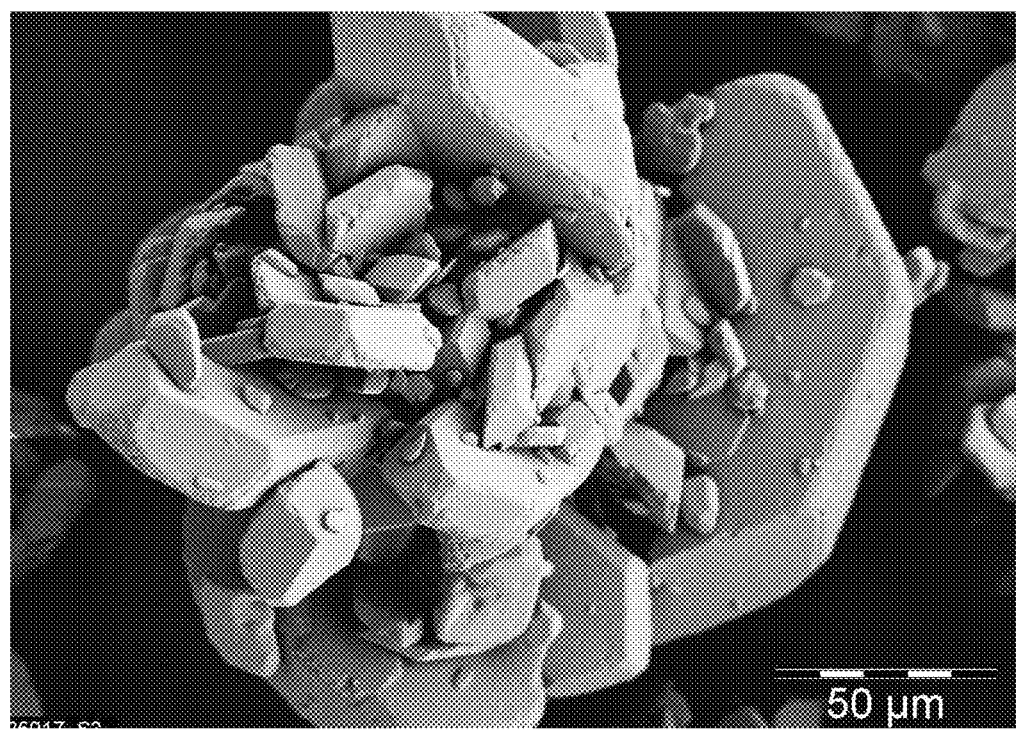

The particles obtained in this step are well flowing aggregates (250 μm average diameter) of crystals with rather smooth surface, as depicted in the SEM images shown in FIG. 4. They can be used as is, or may be easily milled to adjust the desired drug substance particle size.

1. Raw Material Availability

The process may use seed crystals, but they are not necessary. Seed crystals in the present invention assist in controlling the particle size of the resultant Form A crystals. The seed crystals, where used, are milled (to produce a higher particle surface area).

2. Instrument and Methodology Details 2.1 X-Ray Powder Diffraction (XRPD)

2.1.1 Bruker AXS C2 GADDS

X-Ray Powder Diffraction patterns were collected on a Bruker AXS C2 GADDS diffractometer using Cu $K_{alpha}$ radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. A weekly performance check is carried out using a certified standard NIST 1976 Corundum (flat plate).

The beam divergence, i.e. the effective size of the X-ray beam on the sample, was approximately 4 mm. A θ-θ continuous scan mode was employed with a sample—detector distance of 20 cm which gives an effective 2 range of 3.2°-29.7°. Typically the sample would be exposed to the X-ray beam for 120 seconds. The software used for data collection was GADDS for XP/2000 4.1.43 and the data were analysed and presented using Diffrac Plus EVA v15.0.0.0.

Samples run under ambient conditions were prepared as flat plate specimens using powder as received without grinding. Approximately 1-2 mg of the sample was lightly pressed on a glass slide to obtain a flat surface.

2.1.2 Bruker AXS D8 Advance

X-Ray Powder Diffraction patterns were collected on a Bruker D8 diffractometer using Cu $K_{alpha}$ radiation (40 kV, 40 mA), 8-28 goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.6.1 and the data were analysed and presented using Diffrac Plus EVA v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection are:

Angular range: 2 to 42° 2 θ
Step size: 0.05° 2 θ
Collection time: 0.5 s/step

A short method was used for screening samples. Details of the data collection are:

Angular range: 2 to 31° 2θ
Step size: 0.05° 2θ
Collection time: 0.5 s/step

Non-Ambient Conditions

The sample was placed in Anton-Paar TTK 450 chamber at 25° C. The temperature was controlled in-situ through the measurement files: p2853-vt, LRP-1301-39-01.dql, LRP-1301-42-01.dql, LRP-1301-42-02.dql. The sample was heated from 25° C. to 200° C. at 1° C./min. XRPD data were collected from 30° C. to 200° C. every 10° C. Approximately 40 mg of the sample was placed in a Ni-coated sample holder under ambient conditions. The sample was loaded at 25° C.

3. Single Crystal X-Ray Diffraction (SCXRD)

Data were collected on a Rigaku Oxford Diffraction Supernova Dual Source, Cu at Zero, Atlas CCD diffractometer equipped with an Oxford Cryosystems Cobra cooling device. The data was collected using Cu$K_{alpha}$ radiation. Structures were typically solved using either the SHELXS or SHELXD programs and refined with the SHELXL program as part of the Bruker AXS SHELXTL suite (V6.10). Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

4. Proton Nuclear Magnetic Resonance (1H-NMR)

NMR spectra were collected on a Bruker 400 MHz instrument equipped with an auto-sampler and controlled by a DRX400 console. Automated experiments were acquired using ICON NMR v4.0.7 running with Topspin v1.3 using the standard Bruker loaded experiments. For non-routine spectroscopy, data were acquired through the use of Topspin alone.

Samples were prepared in DMSO-d6, unless otherwise stated. Off-line analysis was carried out using ACD Spectrus Processor 2014.

5. Differential Scanning Calorimetry (DSC)

5.1 TA Instruments Q2000

DSC data were collected on a TA Instruments Q2000 equipped with a 50 position auto-sampler. The calibration for thermal capacity was carried out using sapphire and the calibration for energy and temperature was carried out using certified indium. Typically 0.5 3 mg of each sample, in a pin-holed aluminium pan, was heated at 10° C./min from 25° C. to 300° C. A purge of dry nitrogen at 50 mV min was maintained over the sample.

Modulated temperature DSC was carried out using an underlying heating rate of 2° C./min and temperature modulation parameters of ±0.318° C. (amplitude) every 60 seconds (period).

The instrument control software was Advantage for Q Series v2.8.0.394 and Thermal Advantage v5.5.3 and the data were analysed using Universal Analysis v4.5A.

5.2 TA Instruments Discovery DSC

DSC data were collected on a TA Instruments Discovery DSC equipped with a 50 position auto-sampler. The calibration for thermal capacity was carried out using sapphire and the calibration for energy and temperature was carried out using certified indium. Typically 0.5 3 mg of each sample, in a pin-holed aluminium pan, was heated at 10° C./min from 25° C. to 300° C. A purge of dry nitrogen at 50 mV min was maintained over the sample.

The instrument control and data analysis software was TRIOS v3.2.0.3877.

6. Thermo-Gravimetric Analysis (TGA)

6.1 TA Instruments Q500

TGA data were collected on a TA Instruments Q500 TGA, equipped with a 16 position auto-sampler. The instrument was temperature calibrated using certified Alumel and Nickel. Typically 5-10 mg of each sample was loaded onto a pre-tared aluminium DSC pan and heated at 10° C./min from ambient temperature to 350° C. A nitrogen purge at 60 m/min was maintained over the sample.

The instrument control software was Advantage for Q Series v2.5.0.256 and Thermal Advantage v5.5.3 and the data were analysed using Universal Analysis v4.5A.

6.2 TA Instruments Discovery TGA

TGA data were collected on a TA Instruments Discovery TGA, equipped with a 25 position auto-sampler. The instrument was temperature calibrated using certified alumel and nickel. Typically 5-10 mg of each sample was loaded onto a pre-tared aluminium DSC pan and heated at 10° C./min from ambient temperature to 350° C. A nitrogen purge at 25 m/min was maintained over the sample.

The instrument control and data analysis software was TRIOS v3.2.0.3877.

7. Scanning Electron Microscopy (SEM)

Data were collected on a Phenom Pro Scanning Electron Microscope. A small quantity of sample was mounted onto an aluminium stub using conducting double-sided adhesive tape. A thin layer of gold was applied using a sputter coater (20 mA, 120 s).

8. Water Determination by Karl Fischer Titration (KF)

The water content of each sample was measured on a Metrohm 874 Oven Sample Processor at 150° C. with 851 Titrano Coulometer using Hydranal Coulomat AG oven reagent and nitrogen purge. Weighed solid samples were introduced into a sealed sample vial. Approx 10 mg of sample was used per titration and duplicate determinations were made. Data collection and analysis using Tiamo v2.2.

9. Chemical Purity Determination by HPLC

Purity analysis was performed on an Agilent HP1100 series system equipped with a diode array detector and using ChemStation software vB.04.03 using the method detailed below:

TABLE 1

HPLC method for chemical purity determinations

| Parameter | Value |
|---|---|
| Type of method | Reverse phase with gradient elution |
| Sample Preparation | 0.5 mg/ml in acetonitrile:water 1:1 |
| Column | Supelco Ascentis Express C18, 100 × 4.6 mm, 2.7 µm |
| Column Temperature (° C.) | 25 |
| Injection (µl) | 5 |
| Wavelength, Bandwidth (nm) | 255, 90 |
| Flow Rate (ml/min) | 2 |
| Phase A | 0.1% TFA in water |
| Phase B | 0.085% TFA in acetonitrile |

| Timetable | Time (min) | % Phase A | % Phase B |
|---|---|---|---|
| | 0 | 95 | 5 |
| | 6 | 5 | 95 |
| | 6.2 | 95 | 5 |
| | 8 | 95 | 5 |

Figure 5:
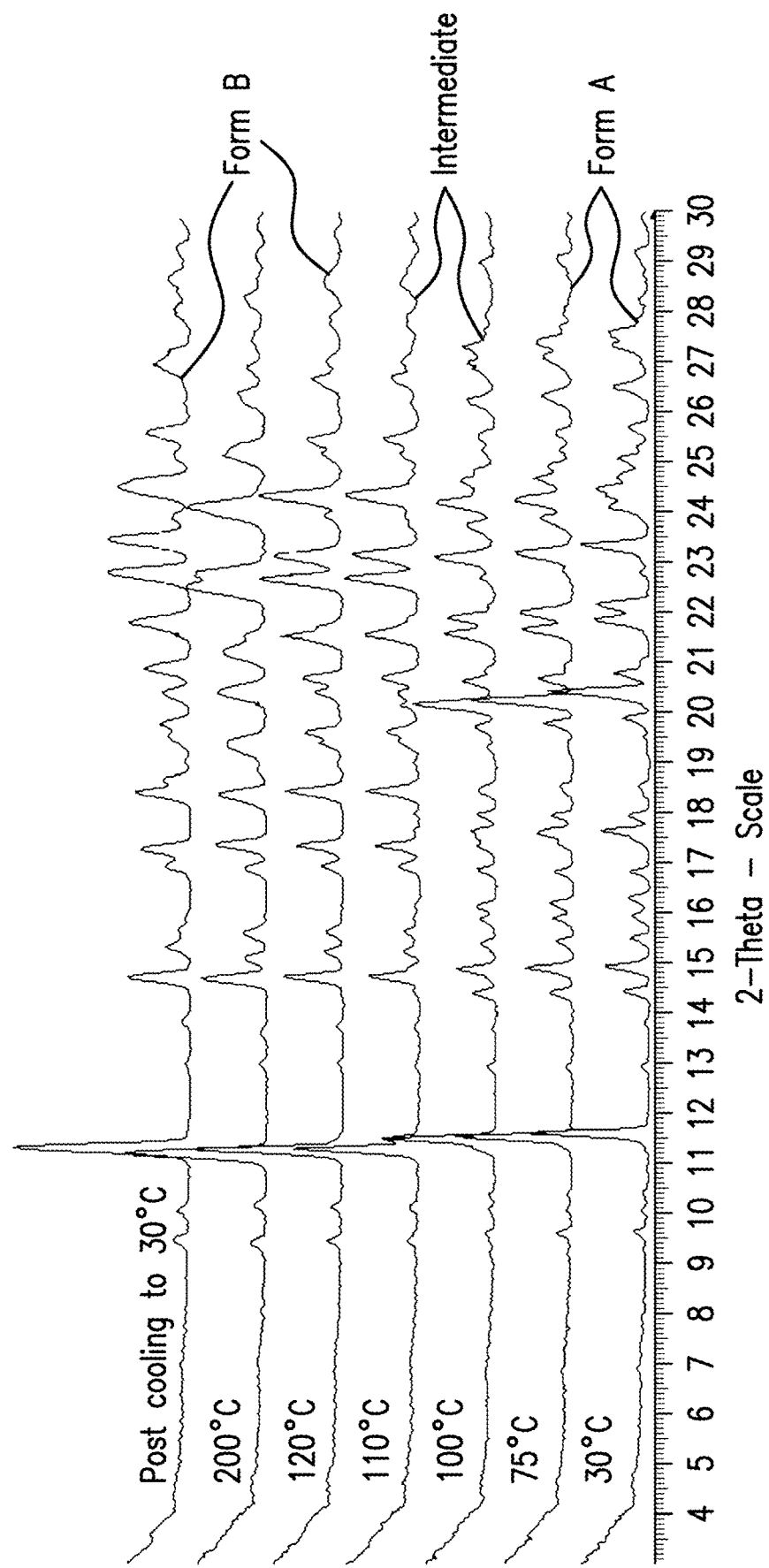
FIG. 5 is a variable temperature XRPD study of Form A 3-[5-amino-4-(3-cyanobenzoyl)-pyrazol-1-yl]-N-cyclopropyl-4-methylbenzamide, showing the transformation into Form B.

The variable temperature XRPD (see FIG. 5) showed that Form A converted to Form B on heating above 100° C. At 200° C., changes (shifts) in peak position in the high 2-theta region were observed. This may be attributed to the thermal expansion effect. However, this thermal effect was reversible and Form B remained unchanged by XRPD after cooling to room temperature.

TABLE 2

Additional DSC experiments on Form A

| | Experiment | | | |
|---|---|---|---|---|
| | Pin holed pan (Onset T) | | Sealed pan (Onset T) | |
| | 1st Endotherm | 2nd Endotherm | 1st Endotherm | 2nd Endotherm |
| 2° C./min | — | 216.4° C. | — | 216.4° C. |
| 10° C./min | 105.7° C. | 216.6° C. | 107.3° C. | 216.2° C. |
| 50° C./min | 111.2° C. | 218.0° C. | 111.5° C. | 218.2° C. |

Figure 6:
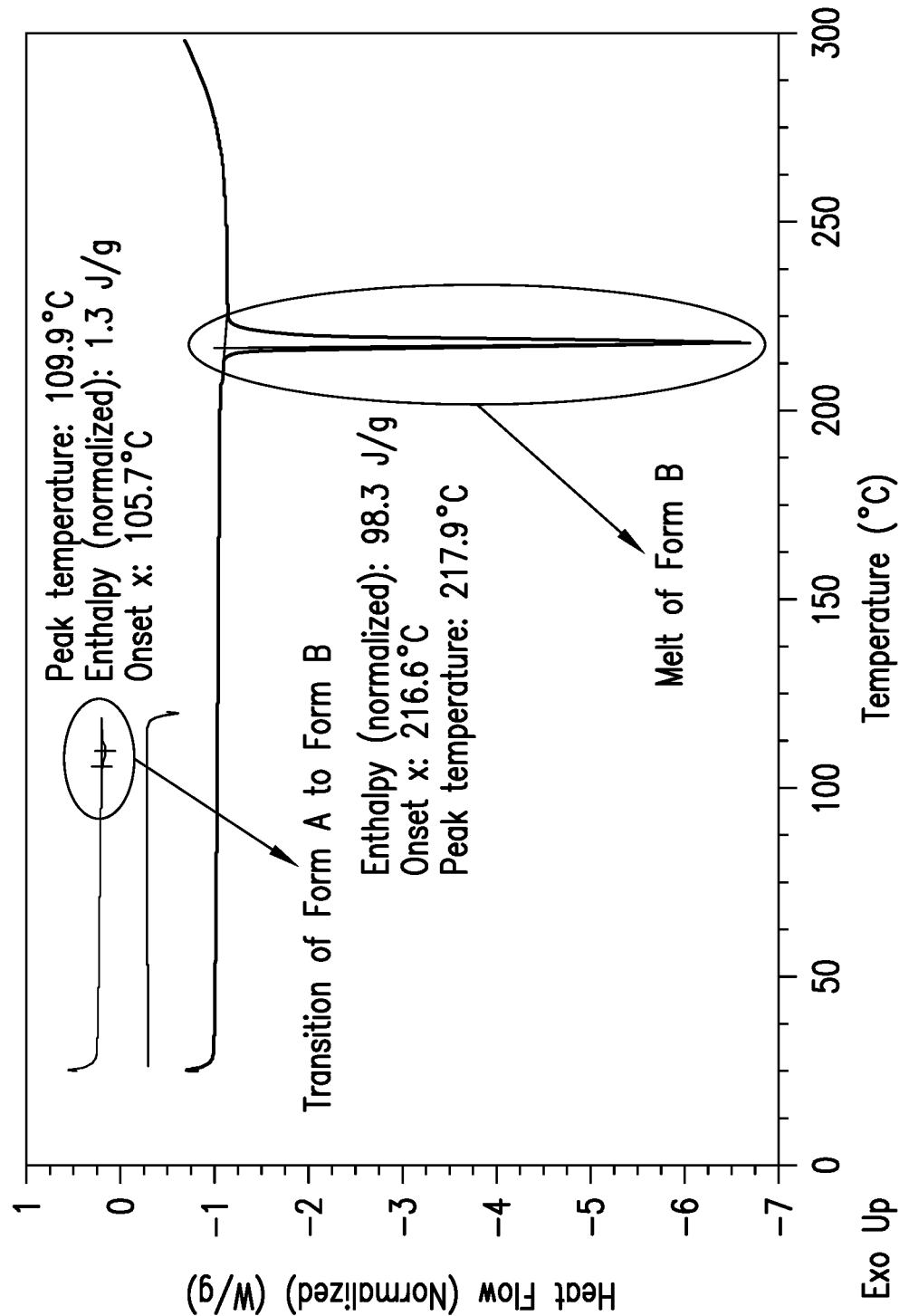
FIG. 6 shows DSC experiments performed on Form A at different heating rates (10° C./min).

The DSC experiments were performed on Form A at different heating rates to determine the nature of the two endotherms observed during the batch characterisation phase (shown in FIG. 6). No significant differences were observed when performing the experiments in pin holed or sealed aluminium pans. At different heating rates, significant differences were observed for the onset of the first endotherm (transition event) indicating it is a possible kinetic event.

The invention claimed is:

1. Form A 3-[5-amino-4-(3-cyanobenzoyl)-pyrazol-1-yl]-N-cyclopropyl-4-methylbenzamide wherein Form A exhibits an X-ray powder diffraction pattern substantially as shown in FIG. 1.

2. A pharmaceutical composition comprising Form A 3-[5-amino-4-(3-cyanobenzoyl)-pyrazol-1-yl]-N-cyclopropyl-4-methylbenzamide of claim 1.

3. Form A 3-[5-amino-4-(3-cyanobenzoyl)-pyrazol-1-yl]-N-cyclopropyl-4-methylbenzamide, wherein Form A has an X-ray powder diffraction pattern measured using Cu Kα radiation with peaks at 2θ=about 9.3, 9.7, 10.2, 10.5, 11.7, 13.0, 14.5, 15.0, 15.5, 16.0, 16.4, 16.0, 17.8, 18.0, 20.0, 20.5, 20.9, 22.0, 22.3, 23.4, 24.2 and 24.5.

4. A pharmaceutical composition comprising Form A 3-[5-amino-4-(3-cyanobenzoyl)-pyrazol-1-yl]-N-cyclopropyl-4-methylbenzamide of claim 3.

5. Form A 3-[5-amino-4-(3-cyanobenzoyl)-pyrazol-1-yl]-N-cyclopropyl-4-methylbenzamide, wherein Form A exhibits an X-ray powder diffraction pattern with characteristic peaks expressed in degrees 2 (+/−0.2° θ) and with substantially similar intensities as shown in Table 1:

| Angle-2-Theta ° | Intensity |
| --- | --- |
| 9.3 | 4.6 |
| 9.7 | 13.7 |
| 10.2 | 5.4 |
| 10.5 | 5.1 |
| 11.7 | 100.0 |
| 13.0 | 6.6 |
| 14.5 | 19.7 |
| 15.0 | 31.6 |
| 15.5 | 14.0 |
| 16.0 | 12.5 |
| 16.4 | 14.9 |
| 16.9 | 12.3 |
| 17.8 | 27.9 |
| 18.0 | 13.9 |
| 20.0 | 17.6 |
| 20.5 | 64.4 |
| 20.9 | 23.1 |
| 22.0 | 39.9 |
| 22.3 | 34.1 |
| 23.4 | 45.8 |
| 24.2 | 26.3 |
| 24.5 | 32.2. |

6. A pharmaceutical composition comprising Form A 3-[5-amino-4-(3-cyanobenzoyl)-pyrazol-1-yl]-N-cyclopropyl-4-methylbenzamide of claim 5.

* * * * *